United States Patent
Yoshii

(10) Patent No.: US 11,045,115 B2
(45) Date of Patent: Jun. 29, 2021

(54) BLINK DETECTION APPARATUS

(71) Applicant: Toyota Jidosha Kabushiki Kaisha, Toyota (JP)

(72) Inventor: Masahiko Yoshii, Susono (JP)

(73) Assignee: Toyota Jidosha Kabushiki Kaisha, Toyota (JP)

(*) Notice: Subject to any disclaimer, the term of this patent is extended or adjusted under 35 U.S.C. 154(b) by 49 days.

(21) Appl. No.: 16/049,095

(22) Filed: Jul. 30, 2018

(65) Prior Publication Data
US 2019/0059790 A1    Feb. 28, 2019

(30) Foreign Application Priority Data

Aug. 31, 2017    (JP) .............................. JP2017-167643

(51) Int. Cl.
| | |
|---|---|
| *A61B 5/11* | (2006.01) |
| *A61B 3/10* | (2006.01) |
| *A61B 5/398* | (2021.01) |
| *A61B 3/14* | (2006.01) |
| *A61B 5/00* | (2006.01) |

(52) U.S. Cl.
CPC .............. *A61B 5/1103* (2013.01); *A61B 3/10* (2013.01); *A61B 3/14* (2013.01); *A61B 5/1128* (2013.01); *A61B 5/398* (2021.01); *A61B 5/7282* (2013.01)

(58) Field of Classification Search
None
See application file for complete search history.

(56) References Cited

U.S. PATENT DOCUMENTS

| | | | |
|---|---|---|---|
| 6,717,518 B1 * | 4/2004 | Pirim ........................ | B60R 1/12 340/576 |
| 2016/0304099 A1 * | 10/2016 | Hatakeyama ........ | A61B 5/1103 |
| 2016/0310060 A1 * | 10/2016 | Li ........................ | A61B 5/1103 |
| 2017/0055868 A1 | 3/2017 | Hatakeyama | |

FOREIGN PATENT DOCUMENTS

| | | |
|---|---|---|
| CN | 106203245 A | 12/2016 |
| JP | 2017-042269 A | 3/2017 |

OTHER PUBLICATIONS

"Automatic Detection of Eyeblinks and Analysis of Eyeblink Waveforms (A Computerized Identification and Data Analysis of Eyeblink EOG Waves)" Hiroaki Yuze et al., Ergonomics, vol. 30, No. 5, pp. 331-337, (1994). (cited in specification).

\* cited by examiner

*Primary Examiner* — Etsub D Berhanu
*Assistant Examiner* — Aurelie H Tu
(74) *Attorney, Agent, or Firm* — Dinsmore & Shohl LLP

(57) ABSTRACT

A blink detection apparatus includes an eyelid state index value measurement unit configured to chronologically measure an eyelid state index value, and a signal processing device. The signal processing device is configured to determine that a blink occurs when a change width of the measured eyelid state index value from a baseline that is a reference value of the eyelid state index value in a case where eyelids are in an opened state exceeds a magnitude of a threshold from the baseline, to count the number of times when the change width of the measured eyelid state index value from the baseline exceeds the magnitude of a tentative threshold from the baseline, and to set the threshold to a tentative threshold at which change in the number of times with respect to the tentative threshold is minimal.

7 Claims, 10 Drawing Sheets

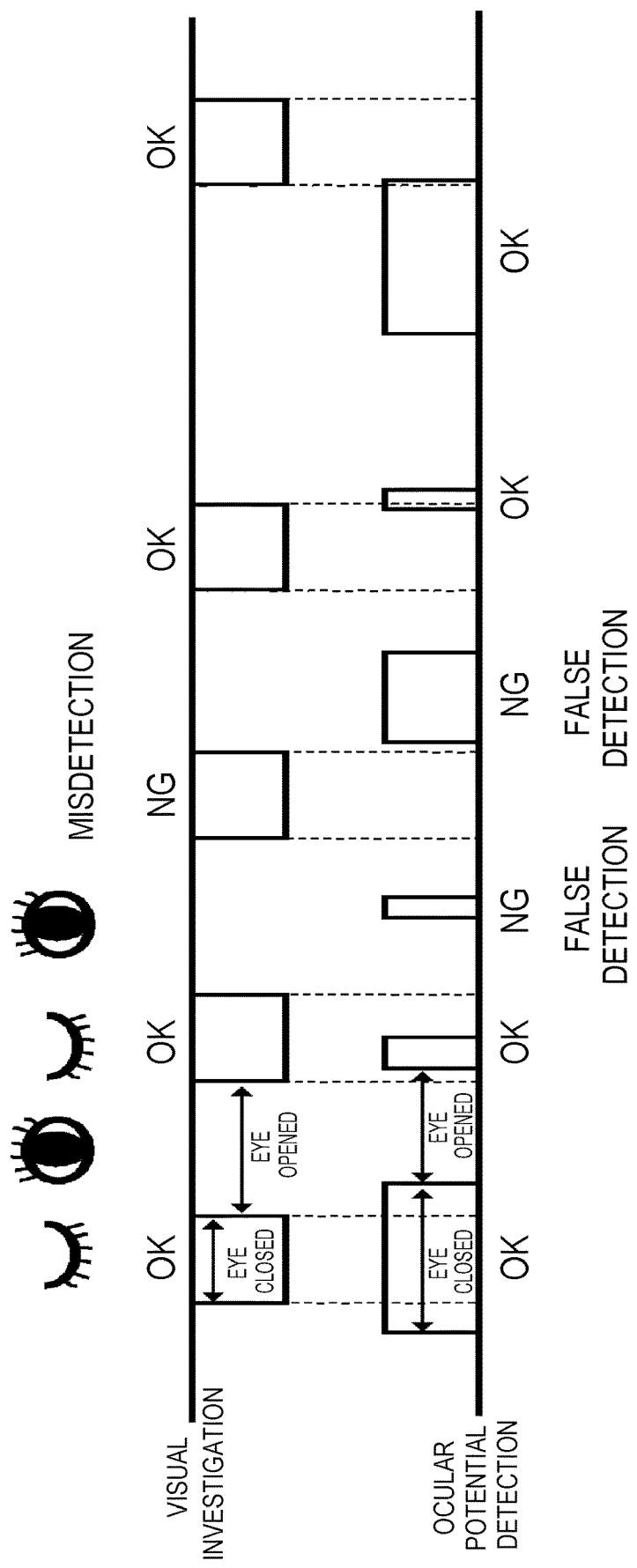

BLINK DETECTION APPARATUS

CROSS-REFERENCE TO RELATED APPLICATIONS

This application claims priority to Japanese Patent Application No. 2017-167643 filed on Aug. 31, 2017, which is incorporated herein by reference in its entirety including the specification, drawings and abstract.

BACKGROUND

1. Technical Field

The present disclosure relates to an apparatus which detects blinks (eyeblinks) of a human, and more in detail, relates to an apparatus which detects blinks in a waveform indicating an eyelid state in an opening-closing motion of eyelids in an electrooculogram (EOG) or the like of a human.

2. Description of Related Art

There are proposed technologies for sensing blinks of a human for the purpose of sensing sleepiness of the human and similar purposes since a blink occurrence frequency of a human and its change are related to the degree of sleepiness of the human. As methods for detecting blinks of a human, there is known an EOG method (electrooculography method) in which the vicinity of an eye is equipped with electrodes and a potential difference (ocular potential) between the retina and the cornea in response to opening-closing of eyelids is detected as well as a method of capturing an image of eyelids of the human and detecting opening-closing of the eyelids from the captured image. In the EOG method, briefly stated, since when an opening-closing motion of the eyelids occurs, as schematically drawn in FIG. 6A, temporary change of the ocular potential occurs, such ocular potential change is obtained from chronologically measured ocular potential data, and thereby, a blink is sensed. Regarding this point, "Automatic Detection of Eyeblinks and Analysis of Eyeblink Waveforms (A Computerized Identification and Data Analysis of Eyeblink EOG Waves)" Hiroaki YUZE; Hideoki TADA, Ergonomics (Japan Ergonomics Society), Vol. 30, No. 5, pp. 331-337 proposes, as an algorithm for automatically detecting such ocular potential change due to eyeblinks, to calculate a differential value of chronological data of the ocular potential, and as shown in FIG. 6B, to detect, as a blink, a waveform part in which the value consecutively exceeds thresholds on the negative side and the positive side within a predetermined time (approximately 0.2 seconds) in the waveform of the differential value of the ocular potential. Japanese Patent Application Publication No. 2017-42269 proposes, in an apparatus which senses eyeblinks in a waveform of chronological data of the differential value of the ocular potential and which detects, as a eyeblink waveform, change of the differential value of the ocular potential when the differential value of the ocular potential changes from an upper threshold to a lower threshold within a predetermined time after it exceeds the upper threshold or when it changes from the lower threshold to the upper threshold within a predetermined time after it goes below the lower threshold, to improve detection accuracy of the eyeblink waveform using, as the upper threshold and the lower threshold, numbers obtained by multiplying coefficients for the thresholds which coefficients are set based on frequency characteristic values indicating frequency characteristics of the differential value of the ocular potential by a standard deviation of the differential value of the ocular potential.

SUMMARY

In the technologies of detecting blinks as above, there is generally made a configuration to chronologically measure an index value indicating an eyelid state or position in an opening-closing motion of eyelids using a sensor for detecting an ocular potential, a camera for capturing an image of the eyelids, or the like, and to determine that a blink occurs when change of the index value at the time when the eyelids are closed relative to the index value (baseline) at the time when the eyelids are opened exceeds a "threshold" (that is, when the index value is displaced upward beyond the "threshold" in the case where the index value at the time when the eyelids are closed is displaced upward from the index value (baseline) at the time when the eyelids are opened, or when the index value is displaced downward beyond the "threshold" in the case where the index value at the time when the eyelids are closed is displaced downward from the index value (baseline) at the time when the eyelids are opened). In such blink detection technologies, as to setting of the "threshold" which is a criterion for blink occurrence, typically in advance, visual observation of an opening-closing motion of eyelids is collated with change of the index value, and a value beforehand specified as the index value at the time when the eyelids are changed from the opened state to the closed state is set as the "threshold" to be used for actual detection of blinks of a subject, for example, in the case of detecting blinks of a driver who is driving a vehicle However, in the case where the threshold preset as above is fixed to be a certain value, even if it is optimal immediately after the start of blink detection processing, there can be a case where it becomes incapable of being used for correct detection of blink occurrence if the baseline which is the reference of the index value varies or a change width of the index value in blink occurrence varies due to a factor of change in physical conditions of the subject and various other factors after actual blink detection processing for the subject is started. Accordingly, to prepare for such a case, it is useful that a device for detecting blinks has a configuration capable of appropriately resetting the threshold even after actual blink detection processing for a subject is started.

Therefore, the present disclosure provides a configuration capable of setting an appropriate threshold even after the start of blink detection processing in a blink detection apparatus which chronologically measures an index value indicating an eyelid state in an opening-closing motion of eyelids and determines that a blink occurs when the index value is displaced upward or downward beyond the threshold.

Moreover, in the apparatus as above, setting of the threshold after the start of blink detection processing is performed in appropriate timing. Therefore, the present disclosure provides an apparatus as above that, is configured to be capable of setting the threshold in proper timing.

A blink detection apparatus according to an aspect of the present disclosure includes an eyelid state index value measurement unit configured to chronologically measure an eyelid state index value indicating a state between an opened state and a closed state of eyelids in an eye of a subject, and a signal processing device. The signal processing device is configured to determine that a blink occurs when a change width of the measured eyelid state index value from a baseline that is a reference value of the eyelid state index value in a case where the eyelids of the subject are in the opened state exceeds a magnitude of a threshold from the baseline, to store the chronologically measured eyelid state index value, to count, with respect to each of a plurality of tentative thresholds, magnitudes of the tentative thresholds being different from one another, the number of times when the change width of the eyelid state index value from the baseline exceeds a magnitude of the tentative threshold from the baseline, for the eyelid state index values that are chronologically measured and stored over a predetermined period, and to set the threshold to a tentative threshold at which change in the number of times with respect to the tentative threshold is minimal.

In the aforementioned aspect, the "eyelid state index value" may be typically an ocular potential, in this case, the "eyelid state index value measurement unit" is configured to be an "ocular potential measurement unit" which measures a potential difference between at least pair of electrodes with which the vicinity of an eye is equipped such that a potential difference between the retina and the cornea in response to opening-closing of the eyelids can be measured in any aspect, and a signal of the potential difference between the electrodes, that is, the ocular potential undergoes AC-to-DC conversion and is used for processing after that. In this case, it is determined, based on the arrangement of the electrodes on a subject, to which of the positive side and the negative side change of the ocular potential is oriented relative to the value of the ocular potential in the case where the eyelids are in the opened state when a blink occurs, that is, when the eyelids become from the opened state to the closed state. It should be understood that this aspect includes the case where the change of the ocular potential at the time when a blink occurs is on the positive side, and also, the case where it is on the negative side. Notably, the "eyelid state index value" may be a time differential value of the ocular potential. Moreover, in another aspect, the "eyelid state index value" may be an index value indicating the degree of opening of eyelids (the distance between the upper eyelid and the lower eyelid or the position of the upper eyelid relative to the lower eyelid) in an image of an eye of a subject. In this case, the "eyelid state index value measurement unit" may include a camera which captures an image of the eye of the subject, and detecting the degree of opening of the eyelids by detecting the positions of the upper eyelid and the lower eyelid in the image of the eye by an arbitrary technique for image processing. It should be noted that in this case, to which of the positive side and the negative side change of the degree of opening of the eyelids in the case where the eyelids become from the opened state to the closed state is oriented depends on the definition of the degree of opening of the eyelids, and in this aspect, includes the case where the change of the degree of opening of the eyelids at the time when a blink occurs is on the positive side, and also, the case where it is on the negative side. Notably, the "eyelid state index value" may be a time differential value of the degree of opening of eyelids. The important thing is that the "eyelid state index value" is displaced when the eyelids become from the opened state to the closed state.

Furthermore, in the aforementioned configuration, the "baseline" may be a reference value of the eyelid state index value in the case where the eyelids of a subject are in the opened state as above, and typically, may be a time average value or the like of the eyelid state index values measured in the case where the eyelids are in the opened state. Here, the eyelid state index values measured in the case where the eyelids are in the opened state may be normally eyelid state index values beforehand measured during a period when the eyelids are visually confirmed to be in the opened state. Notably, when the eyelid state index value is an ocular potential or its time differential value, the baseline may be simply set to be 0 V as the reference value of the eyelid state index value in the case where the eyelids are in the opened state, and it should be understood that this case also belongs to the scope of this aspect. As above, the aforementioned eyelid state index value is typically maintained to be close to the baseline when the eyelids are in the opened state, and when the eyelids become in the closed state, that is, when a blink occurs, changes upward (to the positive side) or downward (to the negative side) beyond the baseline by a certain width. Moreover, the "magnitude of the threshold from the baseline" corresponds to a magnitude of the difference between the baseline and the threshold. Accordingly, in the apparatus of this aspect, it can be determined that a blink occurs when the change width of the eyelid state index value from the baseline exceeds the magnitude of the threshold from the baseline as above. Notably, in an embodiment, since when the eyelid state index value is displaced from the baseline to the positive side in blink occurrence, the change width of the eyelid state index value from the baseline exceeds the magnitude of the threshold from the baseline when the eyelid state index value exceeds the threshold, it may be determined that a blink occurs when the eyelid state index value exceeds the threshold. Moreover, since when the eyelid state index value is displaced from the baseline to the negative side in blink occurrence, the change width of the eyelid state index value from the baseline exceeds the magnitude of the threshold from the baseline when the eyelid state index value goes below the threshold, it may be determined that a blink occurs when the eyelid state index value goes below the threshold.

However, as having already been stated, as to the "threshold" which is the criterion for blink occurrence in the configuration of the blink detection apparatus as in this aspect above, there can be a case where in the state where it remains to be fixed to be a certain value, blink occurrence cannot be detected with excellent accuracy when the baseline varies or the change width of the index value in blink occurrence varies. More in detail, while as to the eyelid state index value, as long as an abnormal event does not occur, when a blink occurs, the eyelid state index value is displaced from the baseline at its maximum by an approximately fixed width (normally, the eyelid state index value docs not vary largely away from the value in blink occurrence), as to such an eyelid state index value which varies as above, when the magnitude of the threshold from the baseline is too small relative to the change width of the eyelid state index value from the baseline which change width corresponds to blink occurrence, this results in a false detection of regarding the change of the eyelid state index value of no blink occurrence as being a blink, and when the magnitude of the threshold from the baseline is too large, this results in a misdetection of blink occurrence.

Therefore, the aforementioned apparatus of this aspect enables update of the threshold to be a proper value in proper timing as above. Specifically, as above, the "signal processing device" is configured to store the chronologically measured eyelid state index value, to count, with respect to each of the plurality of tentative thresholds, magnitudes of the tentative thresholds being different from one another, the number of times when the change width of the eyelid state index value from the baseline exceeds the magnitude of the tentative threshold from the baseline (magnitude of the difference between the baseline and the tentative threshold) over a predetermined period, and to set the threshold to the tentative threshold at which the change in the number of times with respect to the tentative thresholds is minimal. That is, in the "signal processing device", first, the number of times when the change width of the eyelid state index value from the baseline exceeds the magnitude of the tentative threshold from the baseline, so to speak, "the number of times of tentative blink occurrence" is counted for each tentative threshold while the tentative threshold being changed in the eyelid state index values recorded over the predetermined period, next, the tentative threshold at which the change in the number of times of tentative blink occurrence is minimal is detected, this tentative threshold is updated for the "threshold" which is the criterion for blink occurrence.

According to the configuration of the signal processing device above, even after the start of blink detection processing, the "threshold" can be updated to be a more appropriate value using the eyelid state index values having been measured so far. That is, in the configuration of detecting blink occurrence by the change width of the eyelid state index value from the baseline exceeding the magnitude of the threshold from the baseline as in this aspect, as previously touched on, when the magnitude of the threshold from the baseline is too small, this causes many false detections of blink occurrence, and when the magnitude of the threshold from the baseline is too large, this causes many misdetections of blink occurrence, but when the "threshold" is the proper value, if can be considered that both false detections and misdetections of blink occurrence are reduced and the number of times detected is stabilized. Accordingly, the "threshold" that the number of times detected is stabilized at, that is, the tentative threshold at which the change in the number of times of tentative blink occurrence is minimal can be employed as the proper "threshold". Actually, as described in the section of embodiments later, it is indicated that blinks can be detected with excellent, accuracy when the "threshold" selected as above is used.

In the aforementioned aspect, the signal processing device may be configured to count, with respect to each tentative threshold, the number of times when the change width of the eyelid state index value from the baseline exceeds the magnitude of the tentative threshold from the baseline while the tentative threshold is changed or the tentative threshold is scanned at every predetermined width. In this case, in the signal processing device, in an aspect, a tentative threshold at which a difference in the number of times of change of the tentative threshold by the predetermined width is minimal may be selected as the threshold among the tentative thresholds. Moreover, in the signal processing device, in another aspect, a tentative threshold at which a standard deviation in the number of times with respect to a predetermined number (for example, five) of the adjacent tentative thresholds, is minimal may be selected as the threshold among the tentative thresholds. The point is that in the case of generating a histogram of the number of times when the change width of the eyelid state index value from the baseline exceeds the magnitude of the tentative threshold from the baseline with respect to the tentative threshold, the tentative threshold that the histogram is flattest at is sufficient to be selected as the threshold.

Moreover, in the aforementioned aspect, the "predetermined period" for the eyelid stale index value used for setting the threshold may be arbitrarily set by a designer or a user of the apparatus. For example, the "predetermined period" may be the length of a predetermined time. In this case, the "length of the predetermined time" may be act to be the length of time during which a quantity of eyelid state index values with which setting of the threshold can be achieved with excellent accuracy are included. Otherwise, it may be a period until the number of times of blink occurrence that is determined by the signal processing device reaches a predetermined number of times. Here, the "predetermined number of times" may be the number of times of blinks with which setting of the threshold can be achieved with sufficient accuracy. Furthermore, in the aforementioned aspect, the signal processing device may be configured to reset the threshold for each elapse of the predetermined period, and may be configured to be able to update the threshold in proper timing.

As above, in the aforementioned aspect, in the blink detection apparatus which chronologically measures the eyelid state index value and determines that a blink occurs when the change width of the eyelid state index value from the baseline exceeds the magnitude of the threshold from the baseline, when a proper threshold is set, false detections and misdetections of blink occurrence are reduced, and based on the statistical knowledge that in the vicinity of the proper threshold, the counted number of times of blink occurrence is stabilized, the threshold can be updated to be a proper value. According to such an aspect, since when detection of blinks of a driver who is driving a vehicle, detection of blinks of a subject who is working at a desk, or the like is performed, the threshold can be updated to be a proper value in proper timing even when a baseline varies or a change width of an index value in blink occurrence varies after the start of blink detection processing, more excellently accurate detection of blinks can be achieved. Moreover, according to this aspect, since the threshold updating processing can be performed in parallel during performance of blink detection processing, the blink detection processing is not needed to be suspended due to the update of the threshold, and detection of blinks can be performed consecutively for a long time.

Other objects and advantages of this aspect will be apparent from the following description of embodiments of the present disclosure.

BRIEF DESCRIPTION OF THE DRAWINGS

Features, advantages, and technical and industrial significance of exemplary embodiments will be described below with reference to the accompanying drawings, in which like numerals denote like elements, and wherein:

FIG. 3A shows a situation of collating blink occurrence visually confirmed with blink occurrence determined from the ocular potential measured by a sensor. In the figure, "OK" denotes that the blink occurrence visually confirmed can also be detected from the ocular potential (correct answer), and "NG" denotes that the blink occurrence visually confirmed cannot be detected from the ocular potential of the sensor (misdetection) and that a blink is erroneously detected from the ocular potential of the sensor (false detection);

DETAILED DESCRIPTION OF EMBODIMENTS

Hereafter, several embodiments will be described in detail with reference to the appended drawings. In the figures, the same signs denote the same parts.

Configuration of Apparatus

In some embodiments of a blink detection apparatus of the present disclosure, similarly to the case of JP 2017-42269 A, as a basic configuration, an ocular potential of a subject is measured fry the EOG method. As schematically shown in FIG. 1A, it is known that the ocular potential changes in response to an eyelid state in an opening-closing motion of eyelids and that a potential difference occurs to be a substantially fixed width between the case where the eyelids are in a fully opened state and the case where they are in a fully closed state (hereafter, the case where the eyelids are in the fully opened state is supposed to be stated as "opened state" and the case where the eyelids are in the fully closed state is supposed to be stated as "closed state"), since it can be referred to as an index value indicating the eyelid state, that is, an eyelid state index value, when a potential in the case where the eyelids of the subject are in the opened state for chronological data of the ocular potential is set as a reference value, that is, a baseline and when a displacement width of the ocular potential from the same exceeds a magnitude of a threshold which is set to approximately correspond to the potential difference between the opened state and the closed state or to be slightly smaller than the same, it is determined that the eyelids of the subject become in the closed state and that a blink occurs, and thereby, the blink can be detected.

Figure 1A:
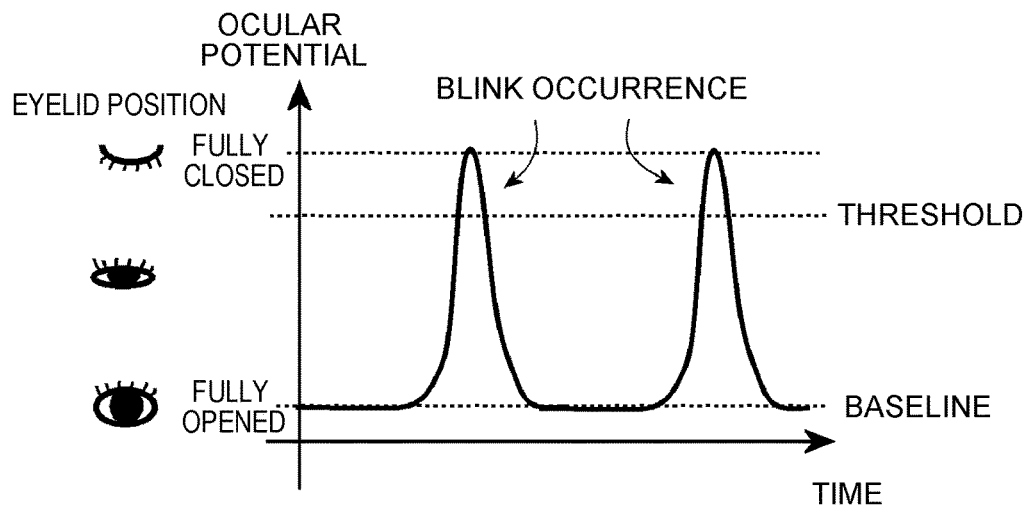
FIG. 1A is a diagram schematically showing change of an ocular potential during blink occurrence obtained by an EOG method.
Figure 1B:
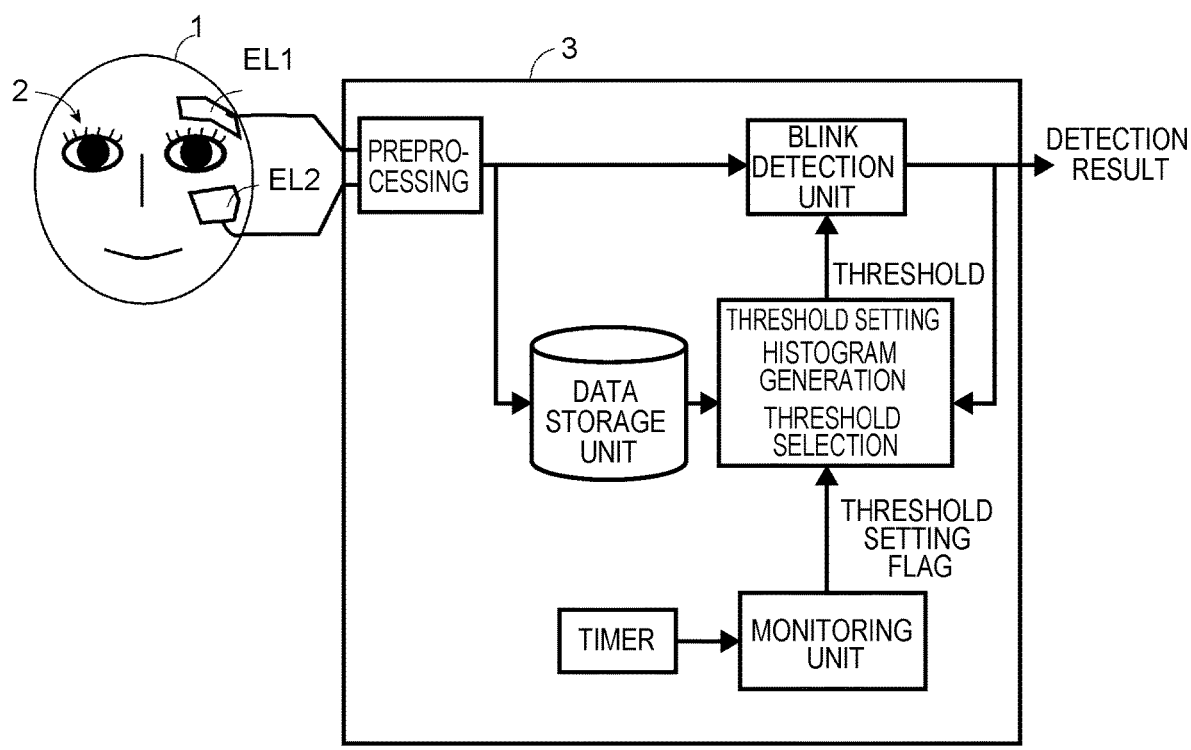
FIG. 1B is a diagram schematically showing a configuration of a blink detection apparatus of the present disclosure.

With reference to FIG. 1B, in a configuration of the blink detection apparatus of the present embodiment, first, at least pair of electrodes EL1, EL2 are pasted around an eye and eyelids 2 of a face 1 of a subject, and a potential difference between the electrodes is sequentially sent as an ocular potential signal to a signal processing device 3. In the signal processing device 3, at a "preprocessing unit", the ocular potential signal from the electrodes sequentially undergoes processing such as digitalizing to be converted into a form adaptable to downstream processing, and the ocular potential signal that has undergone the processing is sent to a "blink detection unit" and a "data storage unit". In the blink detection unit, the ocular potential signal and a threshold are compared with each other in an aspect described later, and blink occurrence is detected. Meanwhile, the ocular potential signal sent to the data storage unit is temporarily stored and accumulated therein, and after that, is used by a "threshold setting unit" for setting the threshold used by the blink detection unit. As described later in detail, the threshold setting unit determines and sets the optimal threshold for detecting blink occurrence using the ocular potential signal obtained over a predetermined period, and the set threshold is referred to by the blink detection unit. Moreover, in the blink detection apparatus of the present embodiment, even during performance of blink detection processing, a configuration to update the threshold at predetermined periods by the threshold setting unit may be adopted, and a "monitoring unit" for monitoring the elapse of the predetermined period may be provided. The monitoring unit may be configured to refer to time from a timer and/or the number of times of blinks detected in the blink detection unit and to give an instruction of performance of threshold setting processing (threshold setting flag) to the threshold setting unit in an aspect described later. Furthermore, the result of blink detection may be sent, for example, to an arbitrary device (not shown) for sleepiness determination, or may be sent, for example, to a display (not shown) to be displayed thereon. The signal processing device 3 may be typically configured to be a computer device, and in the same, a CPU, a storage device, and an input-output device (I/O) which are coupled to one another via a not-shown bidirectional common bus are included in a normal aspect, operation of the individual pans of the blink detection apparatus being achieved by the CPU executing a program.

Figure 6A:
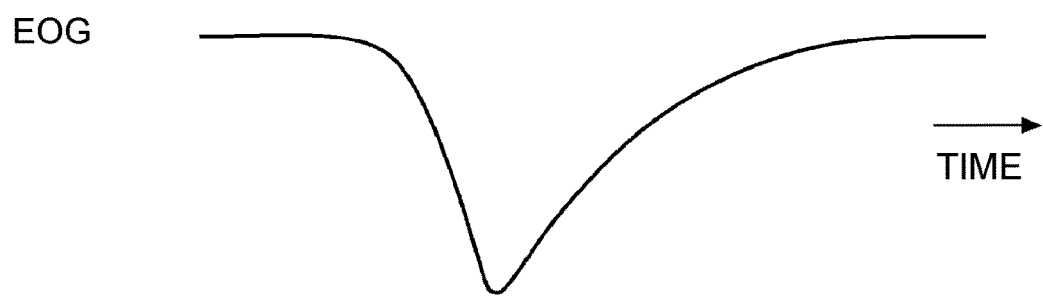
FIG. 6A is a diagram schematically showing change of the ocular potential, in blink occurrence, obtained by the EOG method in the related art. The reason why a change direction of the ocular potential is reverse to that in FIG. 1A is that an arrangement of a positive electrode and a negative electrode is reverse to that in the case of FIG. 1A.
Figure 6B:
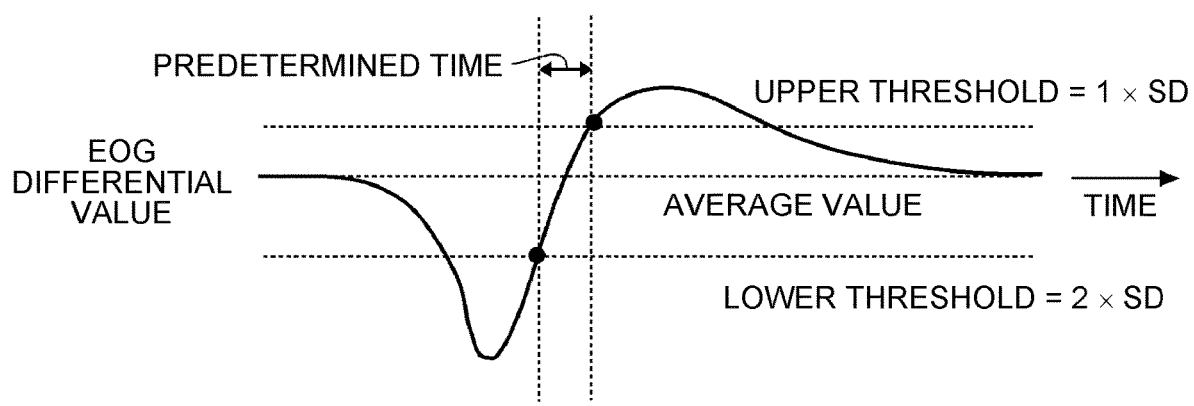
FIG. 6B is a diagram schematically showing a differential value of the change of the ocular potential, in blink occurrence, obtained by the EOG method in the related art. The reason why a change direction of the ocular potential is reverse to that in FIG. 1A is that the arrangement of the positive electrode and the negative electrode is reverse to that in the case of FIG. 1A.

Notably, while in FIG. 1A, as to the ocular potential used as the eyelid state index value, a direction in which the ocular potential in the closed state of the eyelids changes relative to the opened state of the eyelids is on a positive side, since the direction of the change is determined depending on an arrangement of the electrodes EL1, EL2 pasted on the face 1 of the subject, the direction in which the ocular potential in the closed state of the eyelids changes may be on a negative side depending on the arrangement (see FIG. 6A; in such a case, the threshold is set on the lower side of the baseline). The eyelid state index value used for blink detection may be chronological data of ocular potentials themselves as shown in the figure, or may be chronological data of time differential values of them. In this case, since change of the eyelid state index value in blink occurrence occurs on either the positive side or the negative side (see FIG. 6B), the baseline may be set to be substantially zero, and the threshold(s) may be set on any one or both of the positive side and the negative side. Furthermore, the eyelid state index value may be a distance between an upper eyelid and a lower eyelid obtained by detecting positions of the upper eyelid and the lower eyelid by an arbitrary image processing technique from an image of an eye of a subject which image is captured by a camera (not shown). In this case, in the post processing unit, processing until measurement of the distance between the upper eyelid and the lower eyelid from the camera image is performed, chronological data of the distances between the upper eyelid and lower eyelid is sent to the "blink detection unit" and the "data storage unit". In the case where the distance between the upper eyelid and the lower eyelid is used as the eyelid state index value, the distance in the opened state of the eyelids is set as the baseline, and the threshold is set to be the distance (=0) corresponding to the closed state of the eyelids or a value slightly larger than the same. It should be understood that any of the cases belongs to the scope of the present disclosure.

Principles of Detection of Blink and Setting of Threshold

In blink detection by the apparatus of the present embodiment, as above, when the change width of the sequentially measured eyelid state index value from the baseline exceeds the magnitude of the threshold from the baseline, blink occurrence is determined. Regarding this point, since in the ocular potential or the like of a subject which ocular potential is actually used as the eyelid state index value, the change width of the eyelid state index value in blink occurrence has a variation to some extent, and other than the change of the value due to a blink, change due to another factor such as an eyeball motion also occurs, the threshold is adjusted such that a chance that change other than a blink is erroneously detected as a blink is as less as possible, that is, such that false detections are as less as possible, and such that actually occurring blinks can be detected without missing them as less as possible, that is, such that all the blinks can be detected as much as possible with less misdetections.

Moreover, as mentioned in "SUMMARY", even when a certain threshold can be appropriately used for blink occurrence detection immediately after the start, of blink detection processing, there can be a case where it becomes incapable of being used for blink occurrence detection with excellent accuracy due to change in subject's physical conditions afterward and other change in various circumstances. For example, as in waveforms of the ocular potential exemplarily shown in FIG. 7A (waveforms in which the value in the closed state of the eyelids is displaced to the positive side of the value in the opened state of the eyelids), while in the left of the figure, only the waveform parts B in which blinks occur can be selectively detected since all the waveform parts B in which blinks occur exceed the set threshold and variations of the ocular potential other than these go below the threshold, when as in the right of the figure, the baseline rises during performance of blink detection processing due to some factor, variations X of the ocular potential other than blinks also exceed the threshold, end false detections of blinks occur. Moreover, as in waveforms of the ocular potential exemplarily shown in FIG. 7B, while in the left of the figure, only the waveform parts B in which blinks occur can be selectively detected, when in the right of the figure, the baseline falls during performance of blink detection processing due to some factor, waveforms Y which have slightly small amplitudes among the waveform parts B in which blinks occur go below the threshold, which causes misdetections. In order to select only the waveform parts B in which blinks occur as with excellent accuracy as possible even in the case of such circumstance change during performance of blink detection processing, it can be considered that the threshold should be updated to be a proximal value in proper timing without being fixed to be a certain value.

Figure 7A:
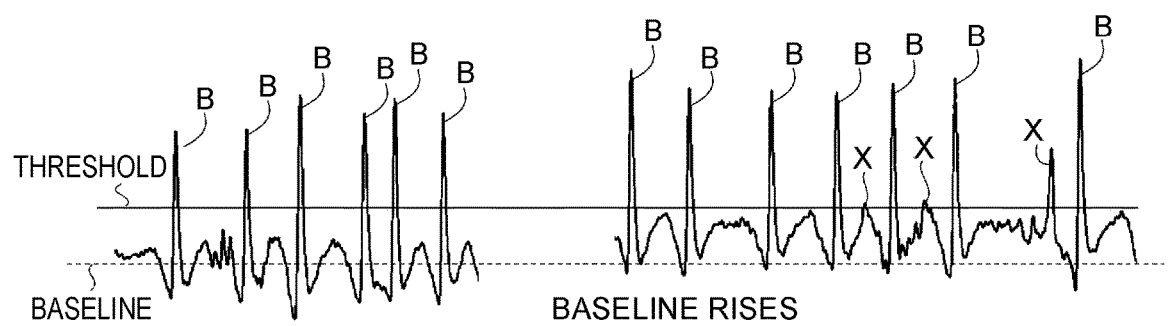
FIG. 7A is a diagram showing a typical time change of the ocular potential along with a threshold which is a criterion of blink detection. There is shown an example in which although in the left stage, ocular potential changes B in which blinks occur can be detected with the set threshold, in the right stage, baseline rises, and false detections X becomes more with the set threshold.
Figure 7B:
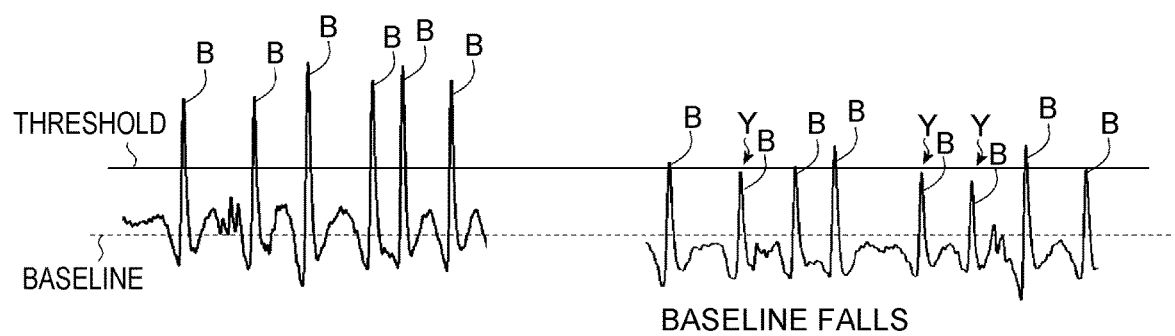
FIG. 7B is a diagram showing a typical time change of the ocular potential along with a threshold which is a criterion of blink detection. There is shown an example in which although in the left stage, ocular potential changes B in which blinks occur can be detected with the set threshold, in the right stage, the baseline falls, and misdetections Y becomes more with the set threshold.

Now, it is assumed that in the waveforms of the ocular potential used as the eyelid state index value exemplarily shown in FIG. 7A and FIG. 7B, scanning is performed from the vicinity of the baseline in a direction in which the magnitude of the threshold becomes large, during the magnitude of the threshold from the baseline being small, false detections are many since variations of the ocular potential other than blinks exceed the magnitude of the threshold as well as the waveform parts B in which blinks occur. Nevertheless, afterward when the magnitude of the threshold from the baseline becomes large to some extent, variations that exceed the magnitude of the threshold from the baseline are only the waveform parts B in which blinks occur, and even when in the vicinity, the threshold somewhat increases or decreases, change in the number of times of variations exceeding the magnitude of the threshold from the baseline becomes little. Then, when the magnitude of the threshold from the baseline further becomes large, even the waveform parts B in which blinks occur do not exceed the magnitude of the threshold from the baseline, and misdetections become many. The reason is that features of waveforms of the ocular potential and the like used as the eyelid state index value are that the amplitudes of the waveform parts B in which blinks occur are substantially uniform (even with some variations) even when the baseline varies, and are larger than variation amplitudes of the ocular potential other than blinks which variation amplitudes overlap with the baseline by a certain width or more. Accordingly, focusing on the features of the waveforms of the eyelid state index value, in a waveform of the eyelid state index value over a certain period, while the magnitude of a temporary threshold (tentative threshold) from the baseline being gradually increased, the number of times of exceeding the magnitude of the tentative threshold from the baseline is counted, a tentative threshold at which change in the number of times of exceeding the magnitude of the tentative threshold from the baseline is most stable is detected, and thereby, it can be considered that this tentative threshold can be used as a proper threshold.

Figure 2A:
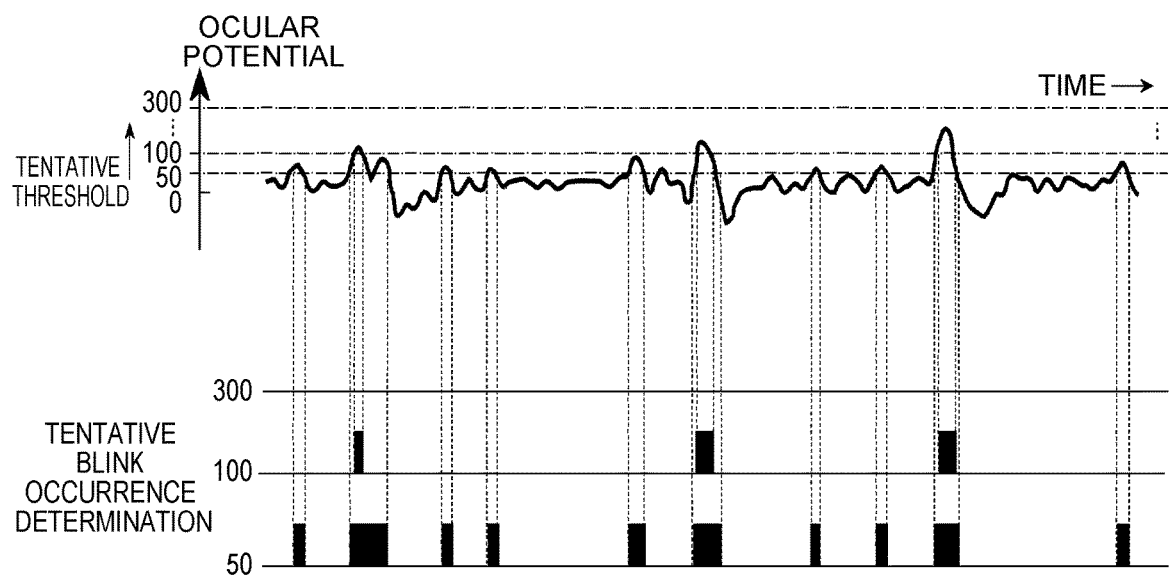
FIG. 2A is a diagram schematically showing a situation of counting the number of times of tentative blinks (the number of times when an eyelid state index value exceeds a tentative threshold) for each magnitude of the tentative threshold with respect to the eyelid state index value (ocular potential) recorded over a predetermined period in accordance with teachings of the present disclosure.

Therefore, setting of the threshold in the present embodiment is performed based on the aforementioned knowledge. Specifically, that is, as schematically shown in FIG. 2A, first, in a waveform of the chronological data of the eyelid state index value such as the ocular potential (in the shown example, a waveform in which the value in the closed state of the eyelids is displaced to the positive side of the value in the opened state of the eyelids), the tentative threshold is being increased from 0 mV at predetermined distances (the distances may be set to be wide when the tentative threshold is small and large, and the distances may be set to be fine within a range in which the tentative thresholds are supposed to be close to the proper threshold), tentative blink occurrence is determined when the magnitude of the eyelid state index value from the baseline exceeds the magnitude of the tentative threshold from the baseline for each tentative threshold, and the number of times thereof is counted. Then, as shown in FIG. 2B, for the number of times of tentative blink occurrence obtained for each tentative threshold, a histogram of the numbers of times of tentative blink occurrence with respect to the tentative thresholds is generated, a tentative threshold that gives the flattest place in a curve ft presenting the number of times of tentative blink occurrence, that is, the minimum min$\Delta$ft in a change curve $\Delta$ft of the number of times of tentative blink occurrence may be selected as the proper threshold.

The flattest place in the curve ft presenting the number of times of tentative blink occurrence, or the minimum min$\Delta$ft in the change curve $\Delta$ft of the number of times of tentative blink occurrence may be detected by an arbitrary technique. In one aspect, a difference $\Delta$ft of the number of times ft($a_t$) of tentative blink occurrence, where the tentative thresholds are $a_0, a_1, \ldots, a_t, \ldots, a_n$, is defined as $$\Delta ft = ft(a_t) - ft(a_{t-1})$$

the tentative threshold at that gives the minimum value min$\Delta$ft of $\Delta$ft may be selected as the appropriate threshold. In another aspect, several standard deviations whose center is ft($a_t$), for example, standard deviations of ft($a_{t-2}$), ft($a_{t-1}$), ft($a_{t+1}$), ft($a_{t+2}$) may be calculated for each of all the tentative thresholds, and the tentative threshold $a_1$ at which the standard deviation is smallest may be selected as the proper threshold (since the standard deviation is smaller as the change is smaller).

Figure 2B:
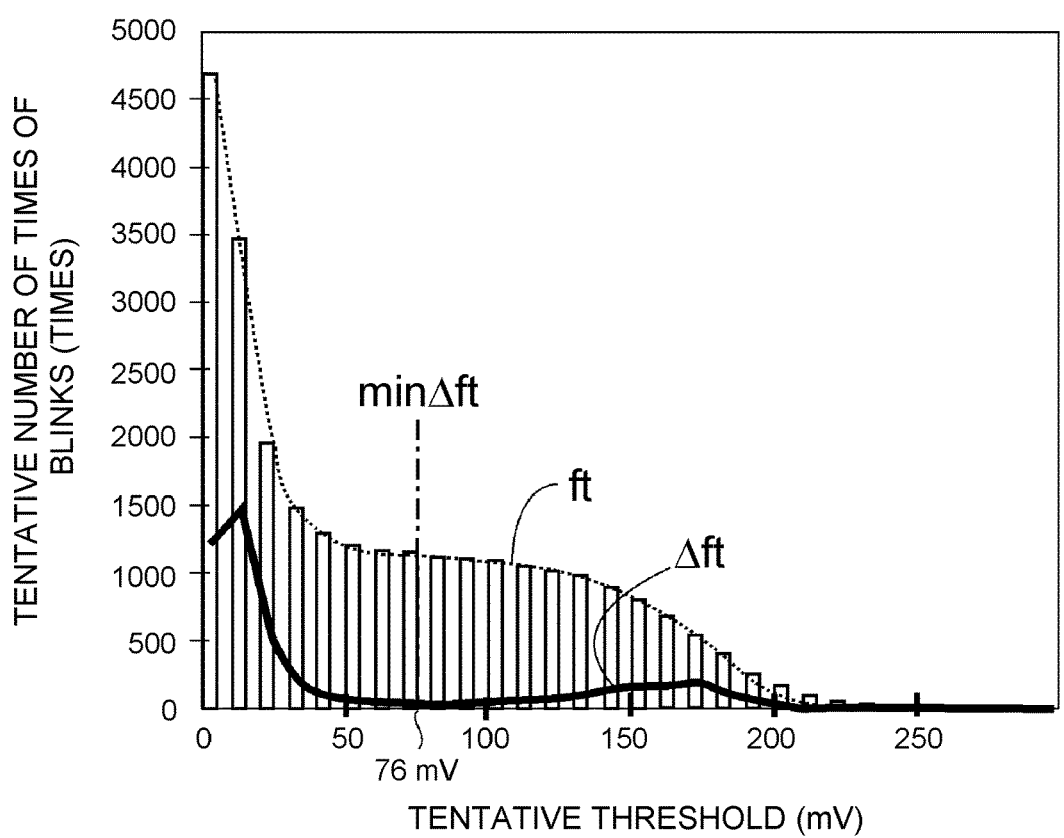
FIG. 2B shows a histogram (bar graph) of the number of times of tentative blinks which histogram is obtained by plotting the numbers of times of tentative blinks with respect to the tentative thresholds, a curve ft presenting the number of times of tentative blinks, and a curve Δft presenting change in the number of times of tentative blinks with respect to the tentative threshold.
Figure 2C:
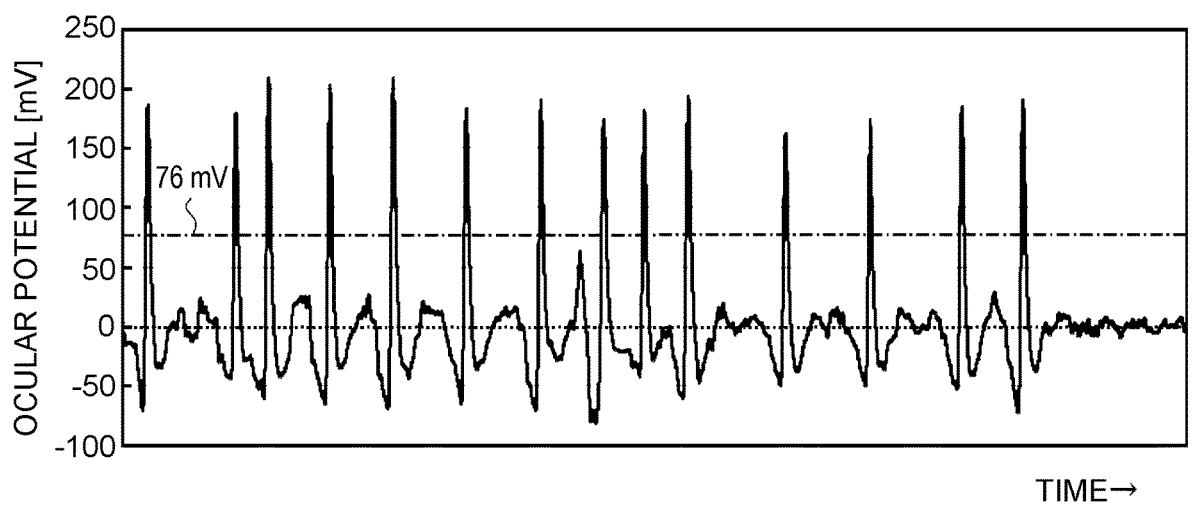
FIG. 2C shows a typical example of time change of the ocular potential, and exemplarily showing that blinks can be detected with excellent accuracy when a tentative threshold at the minimum value in the change in the number of times of tentative blinks with respect to the tentative threshold in FIG. 2B is set to be a threshold.

Notably, the histogram in FIG. 2B is a histogram obtained using an actual example of an ocular potential waveform in which the value in the closed state of the eyelids as the eyelid state index value is displaced to the positive side of the value in the opened state thereof, and the threshold giving min$\Delta$ft was 76 mV. FIG. 2C is a part of the ocular potential waveform used for generating the histogram in FIG. 2B, and as understood from the figure, it can be confirmed that only the waveform of blink occurrence selectively exceeds the threshold when the tentative threshold determined by the aforementioned setting technique of the threshold is set to be the threshold.

Furthermore, in order to investigate validity of the threshold determined by the aforementioned setting technique of the threshold according to the present embodiment, as mentioned below, the blink occurrence detected from the chronological data of the ocular potential of a subject (data in which the value was displaced from the baseline to the positive side in blink occurrence) was collated with the blink occurrence visually confirmed from a video image around an eye of the subject which video image was captured by a video camera to investigate that a threshold properly used for detecting blink occurrence from chronological data of an ocular potential substantially coincided with the threshold determined by the aforementioned setting technique of the threshold.

Figure 3B:
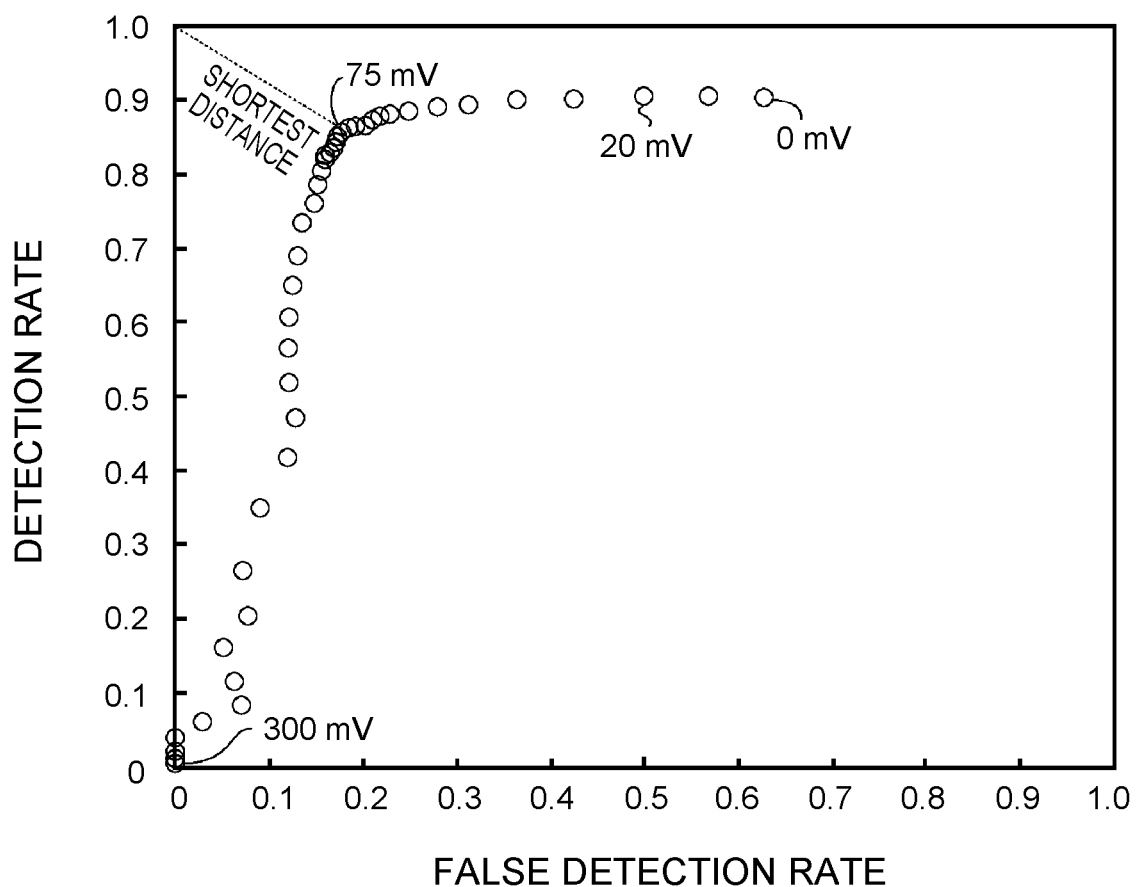
FIG. 3B is a diagram obtained by plotting detection rates with respect to false detection rates, the detection rate (ratio of the number of times of blinks detected from the ocular potential relative to the number of times of blink occurrence visually confirmed) and the false detection rate (ratio of the number of times of false detections relative to the number of times of occasions of being detected as blinks from the ocular potential) being calculated, while the tentative threshold for the ocular potential measured by the sensor being changed. The tentative threshold of the plot nearest from the point with 1.0 of detection rate and 0 of false detection rate is an optimal threshold.

Specifically, the procedure of the investigation was as follows: (i) an image of surroundings of an eye of a subject was captured by a video camera to record this video image simultaneously to measurement of chronological data of an ocular potential of the subject; (ii) periods when blinks occurred (eye closed periods) were visually investigated and detected from the recorded video image of the video camera (upper part of FIG. 3A); (iii) while the threshold being changed from 0 mV to 300 mV in the chronological data of the ocular potential of the subject, periods of exceeding the threshold were detected as periods when blinks occurred (eye closed periods) for each threshold (lower pan of FIG. 3A); (iv) the eye closed periods detected from the chronological data of the ocular potential were collated with the eye closed periods detected through visual investigation of the video image of the video camera for each threshold, when both eye closed periods were at least partially overlapped with each other, a correct answer (OK) was recognized, when the eye closed period detected through visual investigation of the video image of the video camera was not detected from the chronological data of the ocular potential, a misdetection (NG) was recognized, when the eye closed period was detected from the chronological data of the ocular potential in no detection of the eye closed period through visual investigation of the video image of the video camera, a false detection (NG) was recognized, and they were individually counted (upper and lower parts of FIG. 3A); (v) a ratio of the number of correct answers (OK) relative to the number of eye closed periods detected through visual investigation of the video image of the video camera was calculated as a detection rate, and a ratio of the number of false detections relative to the number of eye closed periods detected from the chronological data of the ocular potential was calculated as a false detection rate, for each threshold, which means that a higher detection rate is useful and a lower false detection rate is useful e; and (vi) as shown in FIG. 3B, points for the individual thresholds were plotted, where the horizontal axis denoted the false detection rate and the vertical axis denoted the detection rate, and furthermore, the plot point at the shortest distance from the point with 1.0 of detection rate and 0.0 of false detection rate was specified. It can be understood that the threshold at the plot point at the shortest distance from the point with 1.0 of detection rate and 0.0 of false detection rate is a proper value at which the false detection rate can be suppressed as low as possible and the detection rate can be enhanced as high as possible.

As to the chronological data of the ocular potential from which the aforementioned histogram in FIG. 2B was obtained, the threshold at the plot point at the shortest distance from the point with 1.0 of detection rate and 0.0 of false detection rate obtained by the aforementioned investigation method was 75 mV. This value is substantially equal to the threshold obtained by the threshold setting technique of the present embodiment, 76 mV, and accordingly, the threshold obtained by the threshold setting technique of the present embodiment could be shown to be the proper threshold at which the false detection rate can be suppressed as low as possible, and the detection rate can be enhanced as high as possible.

To be understood is that the threshold setting technique of the present embodiment is a technique obtained by focusing on the feature of the waveform of the eyelid state index value as mentioned above, that is, the feature that the amplitudes of the waveform parts B in which blinks occur are substantially uniform even when the baseline varies, and are larger than variation amplitudes of the ocular potential other than blinks which variation amplitudes overlap with the baseline by a certain width or more, and moreover, that processing of setting the threshold to the tentative threshold at which change in the number of times of tentative blink occurrence is minimal can be performed even when blink detection processing is not suspended. Accordingly, in the apparatus of the present embodiment, the threshold can be updated in proper timing after the start of blink detection processing and even during performance thereof.

Operation of Apparatus

In the apparatus of the present embodiment, as above, blink detection processing (FIG. 4), in the "blink detection unit", of comparing the eyelid state index value with the threshold to detect blink occurrence and threshold setting monitoring processing (FIG. 5A), in the "monitoring unit", for counting the timing when the threshold is updated in the "monitoring unit" may be performed in parallel, and threshold setting processing (FIG. 5B) of setting the threshold in the "threshold setting unit" in accordance with the principle of threshold setting described above may be performed in proper timing.

Figure 4:
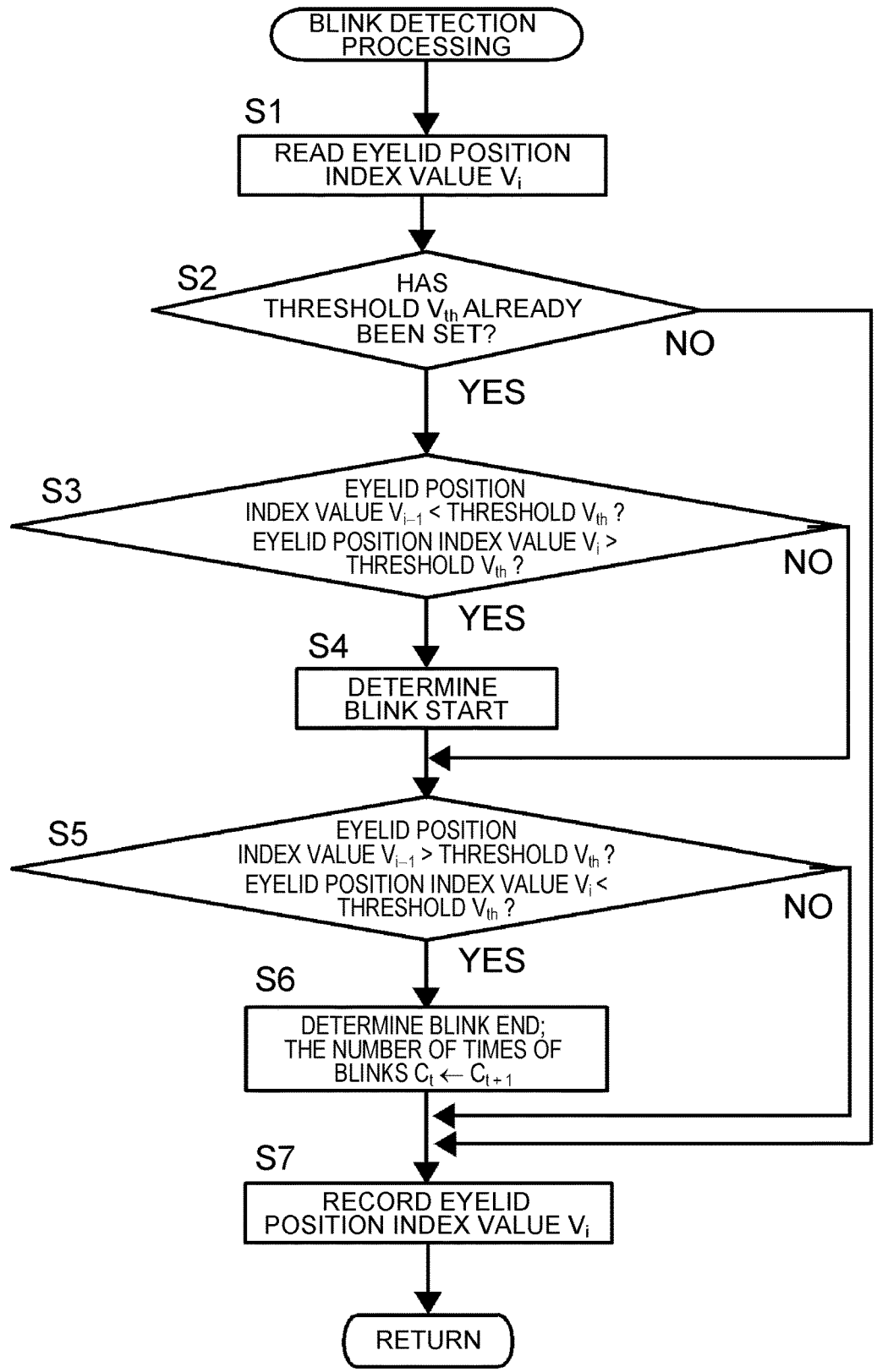
FIG. 4 is a diagram showing, in the form of a flowchart, an example of blink detection processing in the present embodiment.

The blink detection processing which is shown in the form of a flowchart in FIG. 4 and performed in the "blink detection unit" may be performed every time when the eyelid state index value is sequentially read in, after an instruction of the start of the processing by a user of the apparatus. Notably, in the example shown in the figure, the case where the eyelid state index value in the closed state of the eyelids rises above the baseline (average of the eyelid state index values in the opened state of the eyelids) as in FIG. 1A and the baseline is substantially 0 mV is described. In this case, since the eyelid state index value is displaced from the baseline to the positive side in blink occurrence, when an eyelid state index value $V_i$ exceeds a threshold $V_{th}$, a change width of the eyelid state index value $V_i$ from the baseline exceeds the magnitude of the threshold $V_{th}$ from the baseline (it should be understood that the skilled in the art can achieve likewise the case where the eyelid state index value in the closed state of the eyelids falls below the baseline; notably, in this case, when the eyelid state index value $V_i$ goes below the threshold $V_{th}$, the change width of the eyelid state index value $V_i$ from the baseline exceeds the magnitude of the threshold $V_{th}$ from the baseline).

In the process of FIG. 4, specifically, first, the eyelid state index value $V_i$ is read in from the preprocessing unit (step 1), and it is determined whether or not the threshold $V_{th}$ has already been set (step 2). When the threshold $V_{th}$ has not been set, the read eyelid state index value $V_i$ is recorded in the data storage unit as it is (step 7). On the other hand, when the threshold $V_{th}$ has been set as described later in detail, as to the eyelid state index value $V_{i-1}$ read in the previous cycle and the eyelid state index value $V_i$ read in the current cycle, it is determined whether or not the eyelid state index value $V_{i-1}$<the threshold $V_{th}$ and the eyelid state index value $V_i$>the threshold $V_{th}$ (1)

are completed (step 3). When the condition (1) is not completed, the eyelid state is regarded as no change, and the process is put forward soon. When the condition (1) is completed, since this indicates that the eyelid state index value exceeds the threshold and the eyelids are changed from the opened state to the closed state (that the change width of the eyelid state index value from the baseline exceeds the magnitude of the threshold from the baseline), it is determined that a blink starts (step 4). Next, as to the eyelid state index value $V_{i-1}$ read in the previous cycle and the eyelid state index value $V_i$ read in the current cycle, it is determined whether or not the eyelid state index value $V_{i-1}$>the threshold $V_{th}$ and the eyelid state index value $V_i$<the threshold $V_{th}$ (2)

are completed (step 5). When the condition (2) is not completed, the eyelid state is regarded as no change, and the process is put forward soon. When the condition (2) is completed, since this indicates that the eyelid state index value changes from the state of exceeding the threshold to the state of going below the threshold and the eyelids are changed from the closed state to the opened state, it is determined that the blink ends (step 6). Notably, in this stage, the number of times of blinks $C_t$ is incremented by one. Then, the eyelid state index value $V_i$ is recorded in the data storage unit (step 7).

According to the aforementioned series of processes, until the threshold is set, the eyelid state index value is only recorded. Meanwhile, after the threshold is set, when the eyelids are still in the opened state, step 3 and step 5 are passed through with NOs. Then, when the eyelids are changed from the opened state to the closed state and a blink starts, step 3 and step 5 are passed through with YES and NO, respectively, during the closed state of the eyelids continuing, step 3 and step 5 are passed through with NOs, when the eyelids are changed from the closed state again to the opened state and the blink ends, step 3 and step 5 are passed through with NO and YES, respectively, and thus, one time of blink occurrence is detected. After that, the processing is repeatedly performed, thereby, the eyelid state index values are sequentially recorded, in addition, every time when a blink occurs, this is detected, and the results of the number of times and the frequency of blinks, variations of intervals of occurrence thereof, and the like may be used for sleepiness determination and the like.

Figure 5A:
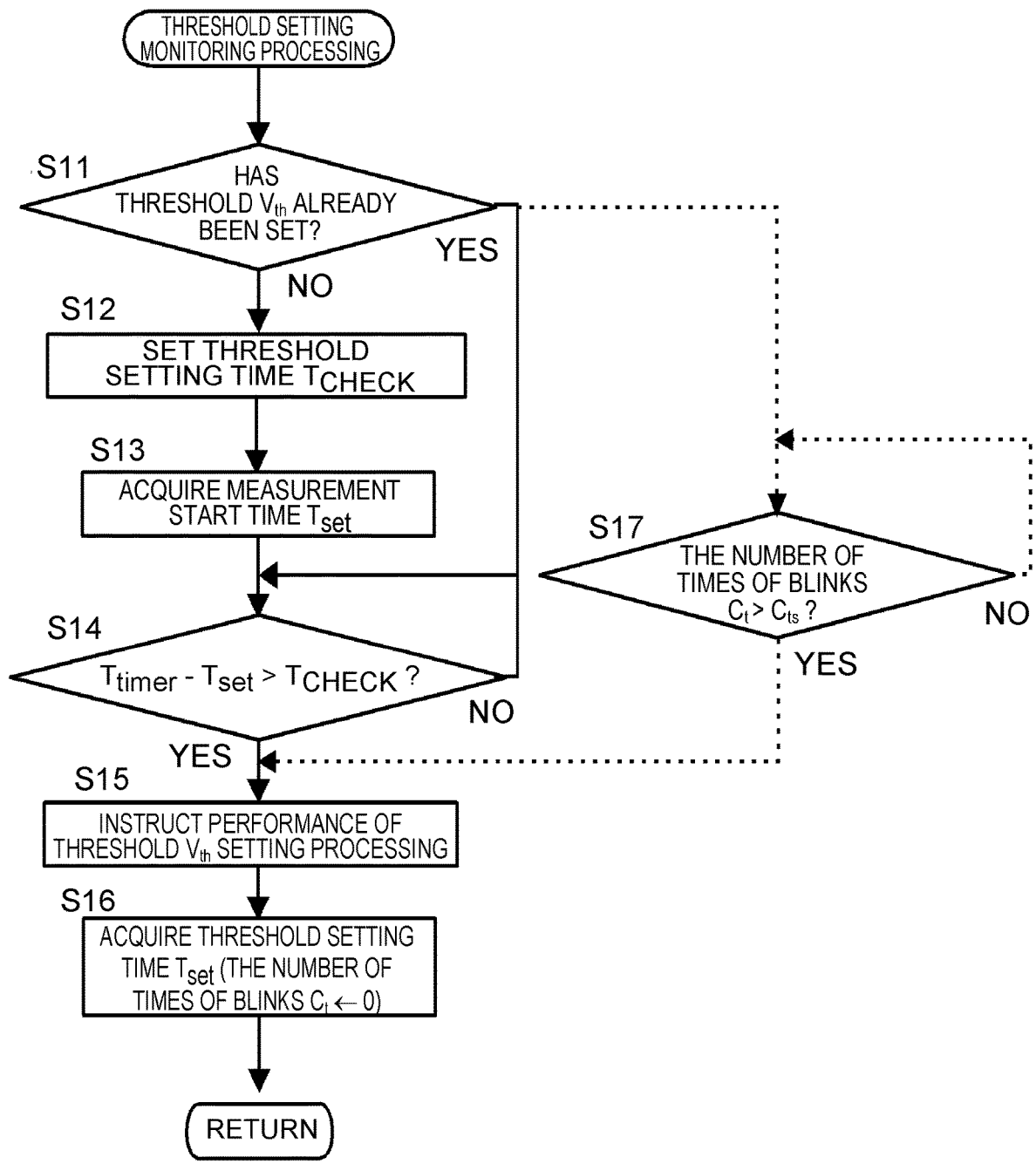
FIG. 5A is a diagram showing, in the form of a flowchart, an example of threshold setting monitoring processing in the present embodiment.

The threshold setting monitoring processing shown in the form of a flowchart in FIG. 5A may be started to be performed simultaneously to the start of the blink detection processing in FIG. 4. In the threshold setting monitoring processing above, briefly stated, processing of instructing performance of processing of setting the threshold used for detecting a blink mentioned above in an aspect mentioned later is performed for each elapse of a predetermined period. In an aspect, of the threshold setting monitoring processing, specifically, first, it is determined whether or not the threshold $V_{th}$ has already been set (step 11), in the stage when the threshold $V_{th}$ has not been set, a threshold setting time $T_{CHECK}$ corresponding to a recording time of the eyelid state index value used for setting the threshold is set (step 12), and a measurement start time is recorded in $T_{set}$ (step 13). After that, time $T_{timer}$ of the timer is referred to, the process is standing by until $T_{timer} - T_{set} > T_{CHECK}$ (3)

is completed (step 14), and during this, the eyelid state index value $V_i$ is recorded in the blink detection processing of FIG. 4. Notably, when the eyelid state index value is the ocular potential as above, the threshold setting time $T_{CHECK}$ may be, for example, 2200 seconds or the like. Then, when the condition (3) is completed, as described later, performance of the setting processing of the threshold $V_{th}$ is instructed (step 15), when the threshold $V_{th}$ has been set, the threshold setting time is recorded in $T_{set}$ (step 16), and the set threshold $V_{th}$ is used in the blink detection processing in FIG. 4. Moreover, when the threshold $V_{th}$ has been set, after that, in the threshold setting monitoring processing, the time $T_{timer}$ of the timer may be referred to, performance of the setting processing of the threshold $V_{th}$ may be instructed every time when the condition (3) is completed, thereby, a new threshold $V_{th}$ may be sequentially determined, and the threshold used for the blink detection processing in FIG. 4 may be sequentially updated.

Figure 5B:
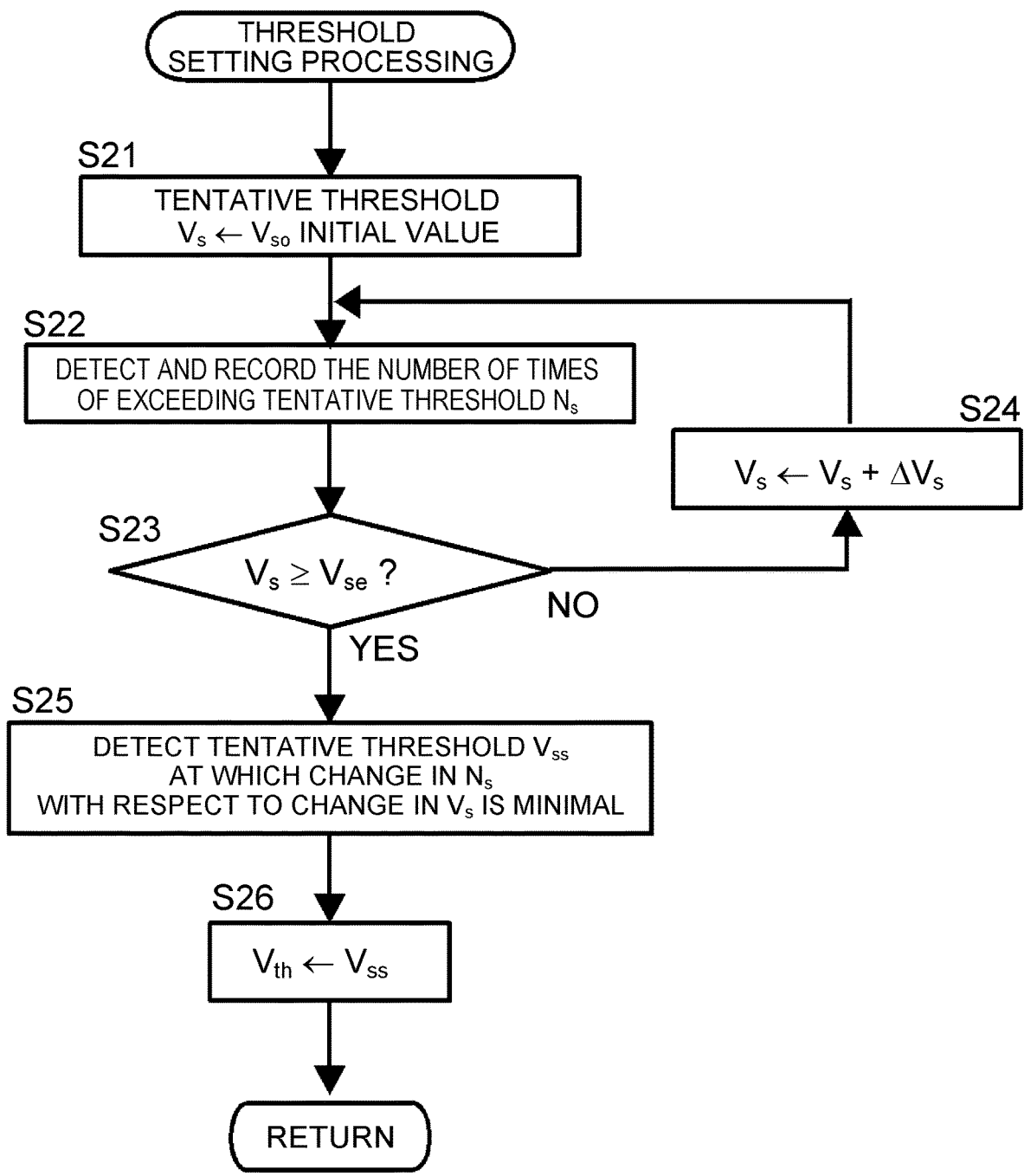
FIG. 5B is a diagram showing, in the form of a flowchart, an example of threshold setting processing in the processing of FIG. 5A.

The threshold setting processing shown in the form of a flowchart in FIG. 5B is performed in response to the instruction of performance (step 15) of the setting processing of the threshold $V_{th}$ by the threshold setting monitoring processing. In the threshold setting processing, first, an initial value $V_{so}$ is set to a tentative threshold $V_s$ (step 21), and for the eyelid state index values $V_i$ sequentially accumulated in the data storage unit during the period when the threshold setting time $T_{CHECK}$ elapses in FIG. 5A, as the number of times of tentative blinks, the number of times when the eyelid state index value $V_i$ exceeds the tentative threshold $V_s$, that is, the number of times $N_s$ when $$V_{i-1} < V_s \text{ and } V_i > V_s \quad (4)$$

is completed is counted and recorded (step 22). Notably, in the example shown in the figure, since the eyelid state index value is displaced from the baseline to the positive side in blink occurrence, when the eyelid state index value $V_i$ exceeds the tentative threshold $V_s$, the change width of the eyelid state index value $V_i$ from the baseline exceeds the magnitude of the tentative threshold $V_s$ from the baseline. After that, until the tentative threshold $V_s$ exceeds an end value $V_{se}$ ($>V_{so}$) (step 23), while the tentative threshold $V_s$ is increased at every predetermined value $\Delta V_s$ (step 24), the number of times $N_s$ when the condition (4) is completed is counted and recorded for each tentative threshold $V_s$ (step 22). Notably, when the eyelid state index value $V_i$ is the ocular potential, for example, settings may be $V_{se}=0$ mV; $\Delta V_s=1$ mV to 10 mV; $V_{se}=300$ mV, and the like. Then, when $V_s \geq V_{se}$ is completed, as stated in the description regarding FIG. 2B, a histogram of the number of times $N_s$ of tentative blink occurrence for the tentative threshold $V_s$ may be generated, the tentative threshold $V_{ss}$ at which the change in the number of times $N_s$ of tentative blink occurrence is minimal may be selected by any of the aforementioned techniques (step 25), and the detected tentative threshold $V_{ss}$ may be set as the new threshold $V_{th}$ (step 26) and may be used for the blink detection processing in FIG. 4.

Now, regarding the performance of the setting processing of the threshold $V_{th}$ for every elapse of the threshold setting time $T_{CHECK}$ in the aforementioned threshold setting monitoring processing of FIG. 5A, the frequencies of blinks depend on individual differences or differences in a person, and the numbers of times of blink occurrence for the threshold setting time $T_{CHECK}$ also depend on individual differences or differences in a person. Meanwhile, in the process of generating the histogram of the number of times $N_s$ of tentative blink occurrence for the tentative threshold $V_s$ in the chronological data of the eyelid state index value, and selecting the tentative threshold $V_{ss}$ at which the change in the number of times $N_s$ of tentative blink occurrence is minimal, accuracies of the histogram and the selected tentative threshold $V_{ss}$ are better as the number of times of blink occurrence in the chronological data of the eyelid state index value which is referred to is more, and in order to attain the sufficient accuracies, it is useful that blinks more than a predetermined number of times occur in the chronological data of the eyelid state index value which is referred to. Accordingly, in the threshold setting monitoring processing of FIG. 5A, in place of updating the threshold $V_{th}$ for each elapse of the threshold setting time $T_{CHECK}$, the threshold $V_{th}$ may be updated every time when the number of times of blink occurrence exceeds a predetermined number. It should be noted that in the case of this aspect, it is needed that the number of times of blink occurrence can be detected with good accuracy to some extent before update of the threshold $V_{th}$ (for example, there is a possibility that it takes a very long time that the number of times of blink occurrence, exceeds the predetermined number when the threshold is too large and blinks can hardly be detected). Therefore, when the threshold is set at first, the threshold setting processing may be performed in the stage after the threshold setting time $T_{CHECK}$ elapses, so that the threshold is once set, and after that, the threshold $V_{th}$ may be updated every time when the number of times of blink occurrence exceeds the predetermined number.

Accordingly, referring to FIG. 5A again, in another aspect of the setting monitoring processing, when the threshold $V_{th}$ has not been set, the processing may be similar to the above, and when the threshold $V_{th}$ has already been set, as indicated by dotted lines in the figure, the process is standing by until the detected number of times of blinks $C_t$ exceeds a predetermined number of times $C_{ts}$ (step 17), and during this, the eyelid state index value $V_i$ is recorded in the blink detection processing of FIG. 4. Notably, when the eyelid state index value is the ocular potential as above, the predetermined number of times $C_{ts}$ may be, for example, 500 or the like. Then, when $C_t > C_{ts}$ is completed, performance of the setting processing of the threshold $V_{th}$ as above is instructed (step 15) and the threshold is set through the processing in FIG. 5B using the chronological data of the eyelid state index value having been accumulated until $C_t > C_{ts}$ is completed, and after the threshold $V_{th}$ is set, the number of times of blinks $C_t$ is reset to be zero (step 16). Afterward, performance of the setting processing of the threshold $V_{th}$ may be instructed every time when $C_t > C_{ts}$ is completed, thereby, a new threshold $V_{th}$ may be determined, and the threshold used in the blink detection processing of FIG. 4 may be updated.

As above, in the present embodiment, briefly stated, in the configuration of detecting, as blink occurrence, an occasion when a change width of the eyelid state index value from the baseline exceeds the magnitude of the threshold from the baseline as described above, the number of times of tentative blink occurrence is counted while a tentative threshold being changed in the chronological data of the eyelid state index value, a histogram of the number of times of tentative blink occurrence with respect to the tentative threshold is generated, and in the histogram, a tentative threshold at which change in the number of times of tentative blink occurrence is minimal is set to be the threshold for detecting blinks. The reason for availability of this setting technique of the threshold is that the waveform of the eyelid state index value has the feature that amplitudes of waveform parts in which blinks occur are substantially uniform even when the baseline varies, and are larger than variation amplitudes of the ocular potential other than blinks which variation amplitudes overlap with the baseline by a certain width or more. Further, it is specially noted that in the technique of threshold setting in the present embodiment, a threshold is not needed to be preset before the start of blink detection processing, and the threshold can be set and updated in proper timing after the start of blink detection processing. According to such a configuration, since when detection of blinks of a driver who is driving a vehicle, detection of blinks of a subject who is working at a desk, or the like is performed, the threshold can be updated to be a proper value in proper timing even when a baseline varies or a change width of an index value in blink occurrence varies after the start of blink detection processing, more highly accurate detection of blinks can be performed consecutively for a long time without the blink detection processing suspended due to the update of the threshold.

While the description above has been made regarding an embodiment of the present disclosure, many modifications and alterations thereof can be easily achieved by the skilled in the art, to whom it will be apparent that the present disclosure is not limited to the embodiment exemplarily shown above but can be applied to various apparatuses without departing from the concept of the present disclosure.

What is claimed is:

1. A blink detection apparatus comprising:
    an ocular potential measurement unit having a pair of electrodes, the ocular potential measurement unit configured to sequentially measure eyelid state index values indicating a state between an opened state and a closed state of eyelids in an eye of a subject; and
    a signal processing device, wherein
    the signal processing device is configured
        to determine, for each measured eyelid state index value, that a blink occurs when a change of the measured eyelid state index value from a baseline that is a reference value of the eyelid state index value in a case where the eyelids of the subject are in the opened state exceeds a magnitude of a threshold,
        to store the sequentially measured eyelid state index values,
        to count a number of times of tentative blink occurrence with respect to each of a plurality of tentative thresholds, the number of times of tentative blink occurrence being the number of times when the change of the eyelid state index value from the baseline exceeds a magnitude of a respective tentative threshold, for each of the eyelid state index values that are sequentially measured and stored over a predetermined period, the magnitudes of the tentative thresholds being different from one another,
        to generate a histogram of the numbers of times of tentative blink occurrence with respect to the tentative thresholds, and
        to set the threshold to a tentative threshold among the tentative thresholds at which a change curve of the histogram is minimal, the change curve representing change in the number of times of tentative blink occurrence measured between consecutively applied tentative thresholds in the histogram.

2. The blink detection apparatus according to claim 1, wherein:
    the predetermined period is a length of a predetermined time; and
    the signal processing device is configured to reset the threshold for each lapse of the predetermined period.

3. The blink detection apparatus according to claim 1, wherein:
    the signal processing device is configured to reset the threshold for each lapse of the predetermined period.

4. The blink detection apparatus according to claim 1, wherein:
    the tentative threshold at which the change curve is minimal is a tentative threshold at which a standard deviation in the number of times of tentative blink occurrence with respect to a predetermined number of adjacent tentative thresholds in the histogram is minimal, among the tentative thresholds.

5. The blink detection apparatus according to claim 1, wherein:
    the ocular potential measurement unit is configured to measure an ocular potential of the subject; and
    the eyelid state index value is the ocular potential.

6. The blink detection apparatus according to claim 1, wherein:
    the ocular potential measurement unit is configured to capture an image of the eye of the subject and to detect a degree of opening of the eyelids in the image of the eye; and
    the eyelid state index value is an index value indicating the degree of opening of the eyelids in the image of the eye.

7. A blink detection apparatus comprising:
    an ocular potential measurement unit having a pair of electrodes, the ocular potential measurement unit configured to sequentially measure eyelid state index values indicating a state between an opened state and a closed state of eyelids in an eye of a subject; and
    a signal processing device, wherein
    the signal processing device is configured
        to determine, for each measured eyelid state index value, that a blink occurs when a change of the measured eyelid state index value from a baseline that is a reference value of the eyelid state index value in a case where the eyelids of the subject are in the opened state exceeds a magnitude of a threshold,
        to store the sequentially measured eyelid state index values,
        to count a number of times of tentative blink occurrence with respect to each of a plurality of tentative thresholds, the number of times of tentative blink occurrence being the number of times when the change of the eyelid state index value from the baseline exceeds a magnitude of a respective tentative threshold, for each of the eyelid state index values that are sequentially measured and stored over a determined period, the magnitudes of the tentative thresholds being different from one another,
        to generate a histogram of the numbers of times of tentative blink occurrence with respect to the tentative thresholds, and
        to set the threshold to a tentative threshold among the tentative thresholds at which a change curve of the histogram is minimal, the change curve representing change in the number of times of tentative blink occurrence measured between consecutively applied tentative thresholds in the histogram,
    wherein the determined period is a period until the number of times of tentative blink occurrence that is determined by the signal processing device reaches a determined number of times; and wherein the signal processing device is configured to reset the threshold for each lapse of the determined period.

* * * * *